(12) United States Patent
Rairkar et al.

(10) Patent No.: US 11,666,528 B2
(45) Date of Patent: Jun. 6, 2023

(54) DRUG IMPLANTS CONTAINING ENZALUTAMIDE AND METHODS OF USE THEREOF

(71) Applicants: The Regents of the University of California, Oakland, CA (US); Alessa Therapeutics, inc., San Carlos, CA (US)

(72) Inventors: Maithili Rairkar, San Francisco, CA (US); Pujan Desai, Oakland, CA (US); Carlos Schuler, San Francisco, CA (US); Keith Hall, San Francisco, CA (US); Pamela Munster, Hillsborough, CA (US); John Maroney, San Francisco, CA (US); Scott Thomas, San Francisco, CA (US)

(73) Assignees: The Regents of the University of California, Oakland, CA (US); Alessa Therapeutics, Inc., San Carlos, CA (US)

( * ) Notice: Subject to any disclaimer, the term of this patent is extended or adjusted under 35 U.S.C. 154(b) by 0 days.

(21) Appl. No.: 17/728,702

(22) Filed: Apr. 25, 2022

(65) Prior Publication Data
US 2023/0080240 A1    Mar. 16, 2023

Related U.S. Application Data

(60) Provisional application No. 63/179,915, filed on Apr. 26, 2021.

(51) Int. Cl.
*A61K 9/00*    (2006.01)
*A61K 47/34*    (2017.01)
*A61K 31/4166*    (2006.01)

(52) U.S. Cl.
CPC ........ *A61K 9/0024* (2013.01); *A61K 31/4166* (2013.01); *A61K 47/34* (2013.01)

(58) Field of Classification Search
CPC .............................. A61K 1/4166; A61K 47/34
See application file for complete search history.

(56) References Cited

U.S. PATENT DOCUMENTS

| | | | |
|---|---|---|---|
| 2017/0114413 | A1 | 4/2017 | Hahn et al. |
| 2017/0119892 | A1 | 5/2017 | Brudno et al. |
| 2019/0307691 | A1 | 10/2019 | Gaillard et al. |
| 2020/0039924 | A1 | 2/2020 | Narayanan et al. |

FOREIGN PATENT DOCUMENTS

| | | |
|---|---|---|
| WO | WO2018/045058 | 3/2018 |
| WO | WO2020/210770 | 10/2020 |

OTHER PUBLICATIONS

Stewart et al., Implantable Polymeric Drug Delivery Devices: Classification, Manufacture, Materials, and Clinical Applications, Polymers, 10, pp. 1-24 (Year: 2018).*

* cited by examiner

*Primary Examiner* — Carlos A Azpuru
(74) *Attorney, Agent, or Firm* — Edward J. Baba; Bozicevic, Field & Francis LLP

(57) ABSTRACT

Provided herein are drug implants comprising enzalutamide for the treatment of disease in a subject. In some cases, the drug implant may comprise a polymer matrix and enzalutamide disposed therein. Additionally provided are methods for manufacturing the drug implants and methods of treating diseases with the implants. In some cases, the drug implant may be used for the treatment of a proliferative disease of the prostate.

21 Claims, 9 Drawing Sheets

DRUG IMPLANTS CONTAINING ENZALUTAMIDE AND METHODS OF USE THEREOF

CROSS-REFERENCE

This application claims the benefit of U.S. Provisional Application No. 63/179,915, filed Apr. 26, 2021, which application is incorporated herein by reference in its entirety.

BACKGROUND OF THE DISCLOSURE

The burden of suffering from prostate cancer in the United States is significant. In 2009, approximately 192,000 men were diagnosed with prostate cancer, and 27,000 men were expected to die from this disease. Approximately 2.2 million living American men have been diagnosed with prostate cancer, and some are living with metastatic disease, a painful and functionally limiting stage of the disease. Prostate cancer is by far the most commonly diagnosed cancer among American men and remains the second leading cause of cancer death in men. Hormonal therapy of prostate cancer includes a wide variety of treatments designed to affect cells whose normal functioning depends on androgens, which include testosterone and dihydrotestosterone, among others. Prostate cancer cells are generally very susceptible to treatments that lower androgen levels or affect the normal action of these hormones.

Enzalutamide is an antiandrogen that may be used to treat prostate cancer. Enzalutamide is a member of the nonsteroidal antiandrogen (NSAA) group of medications and works by blocking the androgen receptor. Enzalutamide has been associated with a number of side effects, which may be due, in part, to the relatively high amounts of enzalutamide that are administered systemically to obtain a therapeutic benefit. Thus, local administration of smaller amounts of enzalutamide may be able to achieve a therapeutic benefit and prevent or reduce side effects or toxicity of systemic enzalutamide administration.

SUMMARY OF THE DISCLOSURE

An unmet need exists for improved drug implants that can be used to deliver a therapeutically active agent (e.g., enzalutamide) directly to a target tissue of a subject. This disclosure meets this unmet need.

In one aspect, a drug implant is provided comprising: a) a biocompatible, non-biodegradable polymer matrix; and b) enzalutamide dispersed in the biocompatible, non-biodegradable polymer matrix. In some cases, the enzalutamide is present in the drug implant at an amount from at least about 10% w/w to about 80% w/w. In some cases, a total dose of the enzalutamide in the drug implant is from about 1 mg to about 10 mg. In some cases, the drug implant releases at least about 0.5 μg/day of the enzalutamide at 6 months after implantation in a subject. In some cases, cumulative release of the enzalutamide in an in vitro model is (i) no more than 2000 micrograms by day 1, no more than 12,000 micrograms by day 60, and no more than 16,000 micrograms by day 120; and is (ii) at least 10 micrograms by day 1, at least 200 micrograms by day 60, and at least 300 micrograms by day 120, wherein the in vitro model comprises incubation of the drug implant in 1% sodium dodecyl sulfate in water at 37° C. with continuous agitation. In some cases, the biocompatible, non-biodegradable polymer matrix is a silicone. In some cases, the silicone is an acetoxy-cured silicone. In some cases, the biocompatible, non-biodegradable polymer matrix is a thermoplastic polyurethane or poly(ethylene vinyl acetate). In some cases, at least 50% of the enzalutamide remains in the biocompatible, non-biodegradable polymer matrix after 100 days of implantation. In some cases, at least 99% by weight of the polymer matrix remains in a target tissue of a subject after implantation for at least 600 days. In some cases, the enzalutamide is in solid form. In some cases, the enzalutamide is in a crystalline form, a semi-crystalline form, or an amorphous form. In some cases, the drug implant has a Shore A hardness of at least 20 durometer when loaded with 60% w/w of the enzalutamide. In some cases, the drug implant is visible by ultrasound when disposed in a target tissue of a subject. In some cases, the enzalutamide has a melting temperature that is greater than a molding or curing temperature of the biocompatible, non-biodegradable polymer matrix. In some cases, the drug implant inhibits modulation of the enzalutamide within the drug implant. In some cases, the modulation comprises degradation. In some cases, the drug implant is elongate. In some cases, the drug implant is cylindrical. In some cases, the drug implant is tubular. In some cases, the drug implant is rod-shaped. In some cases, a diameter of the drug implant is from about 0.1 mm to about 1.5 mm. In some cases, a length of the drug implant is from about 1 mm to about 30 mm. In some cases, a volume of the drug implant is from about 0.1 mm$^3$ to about 30 mm$^3$. In some cases, at least 50% of an outer surface of the drug implant is configured to directly contact a target tissue. In some cases, the drug implant is configured to be implanted into a target tissue or a tissue near or adjacent to the target tissue. In some cases, the target tissue is prostate tissue. In some cases, the drug implant is configured to be delivered to a target tissue using a lumen of a needle or a catheter. In some cases, the drug implant lacks at least one of a sheath, a scaffold, a retention member for retaining the drug implant within a target tissue, or a combination thereof. In some cases, the drug implant further comprises a coating. In some cases, the coating partially covers the drug implant. In some cases, the coating substantially covers the drug implant. In some cases, the coating covers the drug implant. In some cases, the drug implant is sterile. In some cases, the drug implant is disposed in a sterilized package. In some cases, the drug implant consists essentially of the biocompatible, non-biodegradable polymer matrix and the enzalutamide dispersed in the biocompatible, non-biodegradable polymer matrix.

In another aspect, a method of treating a proliferative disease of the prostate of a subject is provided, the method comprising implanting one or more drug implants according to any one of the preceding, into a prostate tissue or a tissue near a prostate. In some cases, the one or more drug implants delivers a therapeutically effective amount of the enzalutamide to the prostate for at least 6 months. In some cases, the proliferative disease of the prostate is prostate cancer or benign prostatic hyperplasia. In some cases, the prostate cancer is castration-sensitive prostate cancer or non-metastatic castration-resistant prostate cancer. In some cases, the enzalutamide is dispersed within the biocompatible, non-biodegradable polymer matrix, prior to the implanting. In some cases, the implanting comprises deploying each of the one or more drug implants to the prostate tissue or the tissue near the prostate through a lumen of a needle or a catheter. In some cases, the implanting occurs via transperineal administration. In some cases, the transperineal administration comprises using a template guided needle. In some cases, a total dose of the enzalutamide administered to the subject is less than a total dose of enzalutamide when administered to a subject by oral administration. In some cases, the total dose of the enzalutamide administered to the subject is less than 100 mg over a period of 6 months. In some cases, the implanting results in a blood plasma concentration of enzalutamide that is less than a blood plasma concentration of enzalutamide obtained when enzalutamide is administered to a subject by oral administration. In some cases, the implanting results in a steady state blood plasma concentration of enzalutamide that is less than about 6 µg/mL. In some cases, the one or more drug implants comprises from 2 to 16 drug implants.

In another aspect, a method of manufacturing a drug implant of any one of the preceding is provided, the method comprising: (a) mixing an amount of uncured polymer with an amount of enzalutamide to form a mixture; (b) molding the mixture to create a molded mixture; and (c) curing the molded mixture by heating the molded mixture for a period of time. In some cases, the amount of enzalutamide is from 10% w/w to 80% w/w of the uncured polymer. In some cases, the polymer is a silicone or a thermoplastic polyurethane. In some cases, the curing of (c) further comprises heating the molded mixture at a temperature from about 150° C. to about 200° C. for about 3 to about 8 minutes. In some cases, the mixture further comprises a solvent. In some cases, the solvent is selected from the group consisting of: pentane, dichloromethane, tetrahydrofuran, heptane, toluene, and hexane. In some cases, the mixture is molded by a transfer molding process or by extrusion through a tube. In some cases, the molding comprises extruding the mixture using a ram extruder or a twin screw extruder. In some cases, the molding comprises injection molding. In some cases, the method further comprises, performing an analysis on the drug implant. In some cases, the analysis is selected from the group consisting of: differential scanning calorimetry (DSC), deployment of the drug implant in surrogate tissue, elution testing, rheology, high pressure liquid chromatography (HPLC), simulated in vivo stability assay, and dynamic mechanical analysis (DMA).

In another aspect, a kit is provided comprising: a sterilized package comprising a drug implant of any one of the preceding claims therein; and instructions for implanting the drug implant into a target tissue of a subject.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Figure 1A:
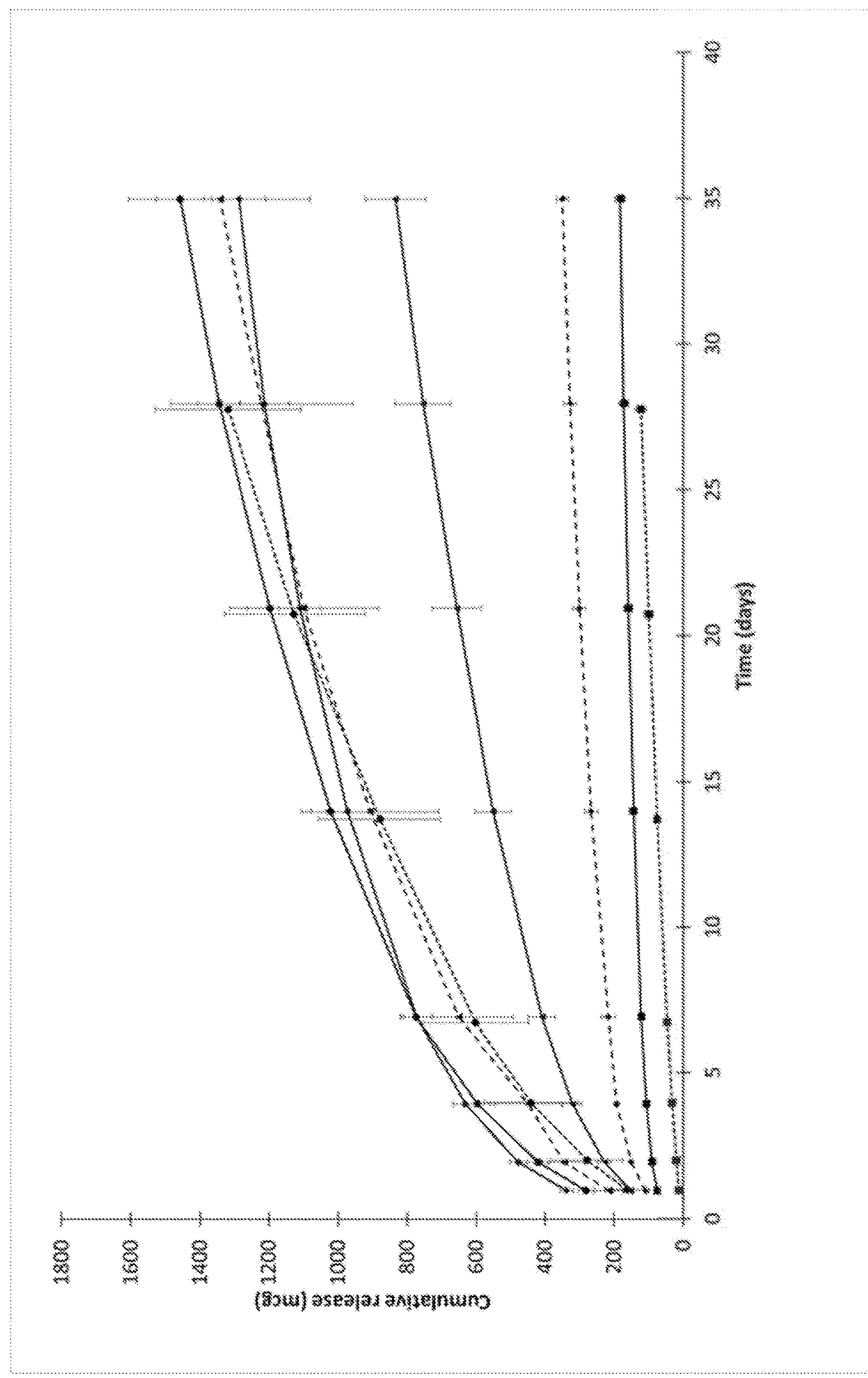
FIG. 1A depicts cumulative release data for drug implants containing enzalutamide at various loading amounts in accordance with embodiments provided herein.

Provided herein are drug implants that are capable of delivering a therapeutically effective amount of enzalutamide directly to a target tissue. Further provided herein are drug implants that, when implanted into a target tissue, result in a high concentration of enzalutamide within the target tissue, and a low concentration of enzalutamide in the systemic circulation (e.g., in the blood plasma). In some cases, the ability of the drug implants provided herein to deliver a therapeutically effective amount of enzalutamide directly to the target tissue, while achieving low concentrations of enzalutamide in the systemic circulation, may reduce or eliminate side effects or toxicity of enzalutamide treatment that would otherwise occur from systemic administration. In addition, delivery of enzalutamide directly to the target tissue by way of the drug implants described herein, ensures that the target tissue receives a therapeutically effective amount of enzalutamide. In further aspects, the drug implants provided herein are capable of being loaded with a large amount of enzalutamide such that the drug implant is capable of sustained release of enzalutamide to the target tissue for extended periods of time. In some aspects, enzalutamide may be dispersed within a polymer matrix of the implant which may provide particular advantages (e.g., faster elution times, higher drug loading within the implant, etc.). In particular aspects, the drug implants provided herein may contain enzalutamide at high concentrations such that a therapeutically effective amount of enzalutamide can be administered directly to prostate tissue for long periods of time (e.g., 6 months or greater) while maintaining low systemic concentrations of enzalutamide.

In various aspects, the drug implants disclosed herein may comprise a polymer matrix and enzalutamide. In particular cases, enzalutamide may be dispersed within the polymer matrix. Preferably, the polymer matrix is biocompatible and non-biodegradable. The drug implants may be implanted into a target tissue, and may release a quantity of enzalutamide over time. The drug implants containing enzalutamide may be effective to treat a disease or a symptom thereof. The disease may be, e.g., a proliferative disease of the prostate, such as prostate cancer or benign prostatic hyperplasia. In some cases, the prostate cancer is castration-sensitive prostate cancer or non-metastatic castration-resistant prostate cancer.

Further provided herein are methods of treating a disease by delivering a drug implant (e.g., containing enzalutamide) of the disclosure to a target tissue of a subject in need thereof in order to deliver a therapeutically effective amount of enzalutamide for extended periods of time. Additionally, methods of manufacturing drug implants and kits including drug implants are provided.

Drug Implants

Provided herein are drug implants (also referred to herein as "implants") suitable for delivering enzalutamide to a target tissue. In some aspects of the disclosure, the implant comprises a polymer matrix (e.g., biocompatible, non-biodegradable) and enzalutamide dispersed therein. The implants may be suitable for treating, e.g., a proliferative disease of the prostate, such as prostate cancer or benign prostatic hyperplasia. In some cases, the prostate cancer is castration-sensitive prostate cancer or non-metastatic castration-resistant prostate cancer.

The polymer matrix may comprise any polymer material. Generally, the polymer material is biocompatible. The term "biocompatible" as used herein refers to a property of a material that allows for prolonged contact with a tissue in a subject without causing toxicity or significant damage. In some cases, a "biocompatible" polymer material is in accordance with the guidelines set forth by the International Organization for Standardization (ISO) 10993-1:2018.

In some aspects, the polymer material may be "non-biodegradable" or "substantially non-biodegradable". The terms "non-biodegradable" or "substantially non-biodegradable", when used in reference to an implant of the disclosure, generally refer to an implant that is incapable or substantially incapable of being decomposed (e.g., by microorganisms, by enzymes (e.g., esterases), by oxidation) over the intended life of the implant. For example, a substantially non-biodegradable implant of the disclosure may have at least 99% by weight of the polymer material remaining two years after implanting the device into a target tissue. In some cases, a "non-biodegradable" implant or polymer may be in accordance with the guidelines set forth by the Standard Guide for Assessment of Absorbable Polymeric Implants (ASTM F2902-16) by ASTM International.

In certain aspects of the disclosure, the polymer matrix may comprise polysiloxane (silicone). The silicone may be any biocompatible silicone. In some cases, the silicone may be a medical grade silicone. In some cases, the silicone may be hydrophobic. In some cases, the silicone may be a United States Pharmacopeia (USP) Class V or USP Class VI certified silicone. In various aspects, the silicone may be an acetoxy-cure silicone. In some cases, the silicone may be a Silbione® silicone adhesive as manufactured by Elkem (e.g., Silbione® Biomedical ADH1 M200; accessible at silicones.elkem.com/EN/our_offer/Product/90061907/_/SILBIONE-BIO-ADH1-M200 as of Sep. 1, 2020).

In other various aspects, the polymer material may be a thermoplastic polyurethane. In some cases, the polyurethane may be one or more of the following polyurethanes manufactured by Lubrizol: PY-PT72AE, PY-PT87AE, PY-PT87AS, PY-PT83AL, and PY-PT43DE20.

In other various aspects, the polymer material may be poly(ethylene vinyl acetate) (PEVA). In some cases, the PEVA may be one or more PEVAs manufactured by Celanese (e.g., under the brand name ATEVA). The vinyl acetate content of the PEVA may be from 9% to 40%. In particular embodiments, the vinyl acetate content is 10%. In other particular embodiments, the vinyl acetate content is 28%. In yet other particular embodiments, the vinyl acetate content is 40%.

The Shore A hardness scale measures the hardness of rubbers. A higher number on the scale refers to a firmer material, whereas a lower number on the scale refers to a softer material. Generally, the polymer material in the drug implant has a Shore A hardness of at least 30-durometer. For example, the polymer material may have a Shore A hardness of at least 30-durometer, at least 40-durometer, at least 50-durometer, at least 60-durometer, or at least 70-durometer. In one aspect, the uncured polymer material may have a Shore A hardness of 30-durometer, and the cured polymer material may have a Shore A hardness of 70-durometer.

The implant may further comprise a therapeutically active agent (e.g., enzalutamide). In some cases, enzalutamide is dispersed or distributed within the polymer matrix. In some cases, the enzalutamide is dispersed or distributed throughout the polymer matrix. In some cases, enzalutamide is uniformly or homogeneously dispersed or distributed within the polymer matrix. In other cases, enzalutamide is heterogeneously dispersed or distributed within the polymer matrix. In other cases, enzalutamide is dispersed or distributed within the polymer matrix in a gradient. In particular aspects, enzalutamide is dispersed or distributed within the polymer matrix at the time of manufacture of the implant (e.g., enzalutamide is mixed with the polymer material prior to curing of the polymer material, as disclosed herein). In some cases, dispersing enzalutamide within the polymer matrix may be advantageous over other drug implants (e.g., those in which the drug is encapsulated in a capsule, or in the lumen of a tube). For example, dispersing enzalutamide within the polymer matrix may allow for higher loading of enzalutamide in the implant, faster elution rates, and the like.

In various aspects of the disclosure, the implant may comprise a therapeutically active agent (e.g., enzalutamide) in an amount from about 0.5% w/w to about 80% w/w. For example, the implant may comprise a therapeutically active agent (e.g., enzalutamide) in an amount of about 0.5% w/w, about 1% w/w, about 5% w/w, about 10% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, about 70% w/w, about 75% w/w, or about 80% w/w. In various aspects, the implant may comprise a therapeutically active agent (e.g., enzalutamide) in an amount of at least about 0.5% w/w, at least about 1% w/w, at least about 5% w/w, at least about 10% w/w, at least about 15% w/w, at least about 20% w/w, at least about 25% w/w, at least about 30% w/w, at least about 35% w/w, at least about 40% w/w, at least about 45% w/w, at least about 50% w/w, at least about 55% w/w, at least about 60% w/w, at least about 65% w/w, at least about 70% w/w, at least about 75% w/w, or at least about 80% w/w. In particular aspects, enzalutamide is present in the implant in an amount of about 0.5% w/w, about 1% w/w, about 5% w/w, 10% w/w, about 30% w/w, about 45% w/w, or about 60% w/w. In some cases, the disclosure provides drug implants loaded with high concentrations of enzalutamide (e.g., about 60% w/w or greater). In some cases, the implant may contain enzalutamide in an amount of at least about 30% w/w. In some cases, the implant may contain enzalutamide in an amount of at least about 45% w/w.

In various aspects of the disclosure, the implant may comprise a therapeutically active agent (e.g., enzalutamide) in an amount from about 5% volume/volume (v/v) to about 60% v/v. For example, the implant may comprise a therapeutically active agent (e.g., enzalutamide) in an amount of about 5% v/v, about 10% v/v, about 15% v/v, about 20% v/v, about 25% v/v, about 30% v/v, about 35% v/v, about 40% v/v, about 45% v/v, about 50% v/v, about 55% v/v, or about 60% v/v. In various aspects, the implant may comprise a therapeutically active agent (e.g., enzalutamide) in an amount of at least about 5% v/v, at least about 10% v/v, at least about 15% v/v, at least about 20% v/v, at least about 25% v/v, at least about 30% v/v, at least about 35% v/v, at least about 40% v/v, at least about 45% v/v, at least about 50% v/v, at least about 55% v/v, or at least about 60% v/v. In particular aspects, enzalutamide is present in the implant in an amount of at least about 30% v/v.

In various aspects, an implant of the disclosure may include enzalutamide in a total amount of at least about 1 mg, for example, from about 1 mg to about 10 mg. In some cases, the total amount of enzalutamide in the implant may be from about 8 mg to about 10 mg. For example, the implant may include enzalutamide in a total amount of about 1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, about 3.0 mg, about 3.1 mg, about 3.2 mg, about 3.3 mg, about 3.4 mg, about 3.5 mg, about 3.6 mg, about 3.7 mg, about 3.8 mg, about 3.9 mg, about 4.0 mg, about 4.1 mg, about 4.2 mg, about 4.3 mg, about 4.4 mg, about 4.5 mg, about 4.6 mg, about 4.7 mg, about 4.8 mg, about 4.9 mg, about 5.0 mg, about 5.1 mg, about 5.2 mg, about 5.3 mg, about 5.4 mg, about 5.5 mg, about 5.6 mg, about 5.7 mg, about 5.8 mg, about 5.9 mg, about 6.0 mg, about 6.1 mg, about 6.2 mg, about 6.3 mg, about 6.4 mg, about 6.5 mg, about 6.6 mg, about 6.7 mg, about 6.8 mg, about 6.9 mg, about 7.0 mg, about 7.1 mg, about 7.2 mg, about 7.3 mg, about 7.4 mg, about 7.5 mg, about 7.6 mg, about 7.7 mg, about 7.8 mg, about 7.9 mg, about 8.0 mg, about 8.1 mg, about 8.2 mg, about 8.3 mg, about 8.4 mg, about 8.5 mg, about 8.6 mg, about 8.7 mg, about 8.8 mg, about 8.9 mg, about 9.0 mg, about 9.1 mg, about 9.2 mg, about 9.3 mg, about 9.4 mg, about 9.5 mg, about 9.6 mg, about 9.7 mg, about 9.8 mg, about 9.9 mg, or about 10.0 mg.

In various aspects of the disclosure, the polymer material may be cured with the enzalutamide present therein. Without wishing to be bound by theory, curing refers to a chemical process that results in the hardening of a polymer material by cross-linking polymer chains. Any method may be used to cure a polymer of the disclosure, including the use of electron beams, heating, and/or the addition of additives. In various aspects of the disclosure, enzalutamide may be mixed with an uncured polymer material prior to curing. In some aspects, the polymer matrix may be at least 95% cured, at least 96% cured, at least 97% cured, at least 98% cured, at least 99% cured, at least 99.9% cured, or 100% cured.

Generally, the polymer material has a molding or curing temperature that is lower than the melting temperature of enzalutamide, e.g., to prevent melting and/or degradation of the drug. In some cases, the polymer material may have a molding or curing temperature that is lower than 195° C., lower than 190° C., lower than 185° C., lower than 180° C., lower than 175° C., lower than 170° C., lower than 165° C., lower than 160° C., lower than 155° C., or lower than 150° C.

In some cases, the polymer is a thermomelt or thermoplastic that becomes moldable at elevated temperature and hardens upon cooling (e.g., polyurethane). In a particular example, enzalutamide may have a melting temperature of about 190° C. to about 192° C., and the polymer may have a molding or curing temperature of less than about 190° C. (e.g., about 170° C.). In some cases, the polymer is a thermoset that is irreversibly hardened by curing (e.g., silicone) which may be promoted by addition of a catalyst and/or heat. In some cases, the polymer material may be cured at room temperature (e.g., about 25° C.). In some cases, the polymer requires exposure to air to cure.

In various aspects of the disclosure, enzalutamide may be present in the implant in solid form. In some cases, solid enzalutamide may be dissolved upon contact with biological fluids (e.g., after implantation into a tissue), and may diffuse out of the implant and into the target tissue. In some cases, enzalutamide is present in the implant in crystalline form, in a semi-crystalline form, or in an amorphous form. In general, the particle size of enzalutamide within the implant may be important for drug content uniformity within the implant. Without wishing to be bound by theory, a small particle size may ensure a uniform distribution within the formulation and between implants upon molding of the formulation. In some cases, the enzalutamide present in the implant may have a median particle size (e.g., D50 particle size) of less than about 10 μm. In some cases, the enzalutamide present in the implant may have a D90 particle size of less than about 15 μm.

Generally, an implant of the disclosure has mechanical properties such that the implant can be successfully deployed into a target tissue. For example, an implant of the disclosure may be sufficiently stiff such that it can be deployed into a target tissue successfully, but not too stiff that it breaks during deployment. It should be understood that the mechanical properties of devices described herein may vary depending on the polymer material used, and may be determined empirically. In some aspects, the implant containing the enzalutamide may have a Shore A hardness of at least 30 durometer.

In various aspects, the implant may have a three-dimensional shape. The three-dimensional shape may be any suitable shape. In some cases, the implant may be cylindrical or substantially cylindrical. In some cases, the implant may be tubular or substantially tubular. In some cases, the implant may be elongate (e.g., may have a length greater than a width). In some cases, the implant may be not hollow. In some cases, the implant may be a rod or rod-like.

In various aspects, the implant may have a diameter. In some cases, a diameter of the implant may be from about 0.1 mm to about 1.5 mm. In some cases, a diameter of the implant may be from about 0.7 mm to about 1.3 mm. In some cases, a diameter of the implant may be from about 0.9 mm to about 1.1 mm. In some cases, a diameter of the implant may be at least about 0.1 mm, for example, at least about 0.1 mm, at least about 0.2 mm, at least about 0.3 mm, at least about 0.4 mm, at least about 0.5 mm, at least about 0.6 mm, at least about 0.7 mm, at least about 0.8 mm, at least about 0.9 mm, at least about 1.0 mm, at least about 1.1 mm, at least about 1.2 mm, at least about 1.3 mm, at least about 1.4 mm, or at least about 1.5 mm. In some cases, a diameter of the implant may be less than about 1 mm, for example, less than about 1 mm, less than about 0.9 mm, less than about 0.8 mm, less than about 0.7 mm, less than about 0.6 mm, less than about 0.5 mm, less than about 0.4 mm, less than about 0.3 mm, less than about 0.2 mm, or less than about 0.1 mm. In some cases, a diameter of the implant may be at least about 0.1 mm. In some case, a diameter of the implant may be at least about 0.8 mm. In some cases, a diameter of the implant may be about 1 mm.

In various aspects, the implant may have a length. In some cases, a length of the implant may be from about 1 mm to about 30 mm. In some cases, a length of the implant may be from about 5 mm to about 25 mm. In some cases, a length of the implant may be from about 10 mm to about 20 mm. In some cases, a length of the implant may be from about 12 mm to about 18 mm. In some cases, a length of the implant may be at least about 1 mm, at least about 2 mm, at least about 3 mm, at least about 4 mm, at least about 5 mm, at least about 6 mm, at least about 7 mm, at least about 8 mm, at least about 9 mm, at least about 10 mm, at least about 11 mm, at least about 12 mm, at least about 13 mm, at least about 14 mm, at least about 15 mm, at least about 16 mm, at least about 17 mm, at least about 18 mm, at least about 19 mm, at least about 20 mm, at least about 21 mm, at least about 22 mm, at least about 23 mm, at least about 24 mm, at least about 25 mm, at least about 26 mm, at least about 27 mm, at least about 28 mm, at least about 29 mm, or at least about 30 mm. In some cases, a length of the implant is at least about 1 mm. In some cases, a length of the implant is at least about 3 mm. In some cases, a length of the implant is about 15 mm. In some cases, a length of the implant may be less than about 30 mm, for example, less than about 30 mm, less than about 29 mm, less than about 28 mm, less than about 27 mm, less than about 26 mm, less than about 25 mm, less than about 24 mm, less than about 23 mm, less than about 22 mm, less than about 21 mm, less than about 20 mm, less than about 19 mm, less than about 18 mm, less than about 17 mm, less than about 16 mm, less than about 15 mm, less than about 14 mm, less than about 13 mm, less than about 12 mm, less than about 11 mm, less than about 10 mm, less than about 9 mm, less than about 8 mm, less than about 7 mm, less than about 6 mm, less than about 5 mm, less than about 4 mm, less than about 3 mm, less than about 2 mm, or less than about 1 mm.

In various aspects, the implant may have a volume. In some cases, the volume of the implant may be from about 0.1 mm$^3$ to about 30 mm$^3$. For example, the volume of the implant may be about 0.1 mm$^3$, about 0.5 mm$^3$, about 1 mm$^3$, about 5 mm$^3$, about 10 mm$^3$, about 15 mm$^3$, about 20 mm$^3$, about 25 mm$^3$, or about 30 mm$^3$. In some cases, the volume of the implant may be about 10 mm$^3$.

In various aspects, the implant may lack a coating, covering, or a sheath. For example, in some cases, a portion of the outer surface of the implant may not be coated or covered such that the outer surface of the uncoated or uncovered portion of the implant is directly exposed to or directly contacts the biological environment (e.g., a target tissue, a biological fluid) after implantation. In some examples, the entire outer surface or substantially the entire outer surface of the implant is uncovered or uncoated such that the entire outer surface or substantially the entire outer surface of the implant is directly exposed to or directly contacts a biological environment after implantation. In other cases, less than the entire outer surface of the implant is directly exposed to or directly contacts a biological environment after implantation. For example, in some cases, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% of the outer surface of the implant is directly exposed to or directly contacts a biological environment after implantation. In some cases, at least about 50% of the outer surface of the implant is directly exposed to or directly contacts a biological environment after implantation. In some cases, the implant may lack a sheath, a scaffold, a retention member, a retention frame, or any other additional means for retaining the implant within the target tissue. In some cases, the implant may consist essentially of the polymer matrix and the therapeutically active agent (e.g., enzalutamide) dispersed therein.

In some cases, the implant may comprise a coating. In some cases, the coating may cover the implant. In some cases, the coating may partially cover the implant. In some cases, the coating may substantially cover the implant. In some cases, the implant may comprise a core made of a first polymer material, and a coating of a second polymer material. In a non-limiting example, an implant of the disclosure may include a non-silicone core, surrounded by a silicone coating. In some cases, an implant of the disclosure does not comprise a metal.

In various aspects, the implant may prevent modulation of the enzalutamide contained therein when the implant is implanted into a subject. Modulation can include, but is not limited to, degradation, chemical modification, and the like. For example, the biological environment of a tissue may include degradants that are capable of degrading the drug (e.g., esterases, amidases). In some cases, the implant may protect the therapeutically active agent from degradation by preventing the degradant from penetrating the implant. In various aspects, in vitro stability testing may be performed to determine the protective effect of the implant on the therapeutically active agent contained therein. In such cases, the therapeutically active agent may be capable of diffusing out of the implant while maintaining in vivo stability within the implant. In various aspects, the ability of a degradant to degrade a therapeutically active agent within the implant may be determined by a simulated in vivo stability assay. In a non-limiting example, an implant of the disclosure comprising a therapeutically active agent may be incubated in a solution comprising a degradant (known to degrade the therapeutically active agent). After a period of incubation, the therapeutically active agent may be extracted from the implant and degradation peaks may be measured (e.g., by high-performance liquid chromatography (HPLC)).

In various aspects of the disclosure, an implant of the disclosure may be configured to be delivered directly to a target tissue of a subject. In some cases, the target tissue may be prostate tissue. In some cases, an implant of the disclosure may be configured to be delivered to a tissue adjacent to or nearby a target tissue. In some cases, the therapeutically active agent may diffuse out of the implant in a controlled manner and act directly on the target tissue.

In various aspects, an implant of the disclosure may be configured to remain within the target tissue for a period of time. In some cases, an implant of the disclosure may be configured to remain within the target tissue indefinitely (e.g., is never removed). In some cases, two or more implants of the disclosure may be implanted into the target tissue. For example, 2, 3, 4, 5, 6, 7, 8, 9, 10, 11, 12, 13, 14, 15, 16, 17, 18, 19, 20 or more than 20 implants may be implanted in the target tissue. In some cases, the two or more implants may be implanted in different sites of the target tissue (e.g., to deliver drug to different sites of the target tissue). In some cases, the two or more implants may be implanted in close proximity to one another within the target tissue. In some cases, one or more initial implants may be implanted, and additional implants may be later implanted after the drug has been exhausted from the initial implants.

For example, one or more additional implants may be implanted after a drug has stopped, or substantially stopped, eluting from one or more initial implants. In some cases, an implant of the disclosure may be visible by ultrasound when disposed within the target tissue of the subject. In such cases, the position of the implant may be monitored non-invasively. In some cases, the implant may be sterilized prior to implantation into a subject. In some cases, the implant is sterilized via gamma sterilization.

In various aspects, an implant of the disclosure may be capable of delivering a sustained release of enzalutamide for a period of time. For example, an implant of the disclosure may be capable of sustained release of the enzalutamide. "Sustained release" as used herein refers to the capability of the implant to release an amount of drug for an extended period of time after implantation into a target tissue. In some cases, an implant of the disclosure may be capable of delivering an amount of drug to a target tissue for at least 6 months, at least 9 months, at least 12 months, at least 18 months, or at least 24 months. In particular cases, an implant of the disclosure may be capable of delivering at least 0.5 μg/day of enzalutamide for at least 6 months after implantation into a target tissue (e.g., prostate tissue or tissue adjacent or near the prostate). In some cases, an implant of the disclosure may be capable of delivering at least 0.1 μg/day of enzalutamide (e.g., to a target tissue) for up to 24 months after implantation into a target tissue (e.g., prostate tissue or tissue adjacent or near the prostate).

In some cases, a drug implant of the disclosure may exhibit one or more, or all of the following characteristics: cumulative release of the enzalutamide in an in vitro model of no more than 2,000 micrograms by day 1, cumulative release of the enzalutamide in an in vitro model of no more than 12,000 micrograms by day 60, and cumulative release of the enzalutamide in an in vitro model of no more than 16,000 micrograms by day 120. In some cases, a drug implant of the disclosure may exhibit one or more, or all of the following characteristics: cumulative release of the enzalutamide in an in vitro model of at least 10 micrograms by day 1, cumulative release of the enzalutamide in an in vitro model of at least 200 micrograms by day 60, and cumulative release of the enzalutamide in an in vitro model of at least 300 micrograms by day 120. The in vitro model may include incubation of the drug implant in 1% sodium dodecyl sulfate (SDS) in water at 37° C. for the specified time period with continuous agitation.

Methods for Manufacturing Drug Implants

Further provided herein are methods for manufacturing the implants described herein. A non-limiting example of a method for manufacturing a drug implant of the disclosure may be as provided in Examples 1-3.

In some aspects, the methods may involve mixing an amount of polymer material with an amount of enzalutamide to form a mixture. In some cases, the polymer is a thermoset and the enzalutamide is mixed into the uncured polymer material. In some cases, the polymer is a thermoplastic and the enzalutamide is mixed into a solution or melt of the polymer material. The methods may further involve molding the mixture to create a molded structure. The molded structure may be formed by molding the mixture in a mold (e.g., transfer molding process), by extruding the mixture (e.g., through a tube), or by any other process. In the case of a thermoset, the methods may further involve allowing the molded mixture to cure for a period of time with or without elevated temperature. In some cases, the polymer material may be any biocompatible silicone provided herein. In an exemplary aspect, the silicone may be Silbione® ADH1 M200. In the case of a thermoplastic, the mixture may be molded as described at elevated temperature and cooled to solidify the polymer. In some cases, the thermoplastic may be any biocompatible polyurethane provided herein. In some cases, the molding includes extruding the mixture using a ram extruder or a twin screw extruder. In some cases, the molding includes injection molding.

In some aspects, the mixture may further comprise a solvent. Non-limiting examples of solvents that may be used include pentane, heptane, toluene, dichloromethane, tetrahydrofuran, and hexane. A solvent may be used to, e.g., reduce the viscosity of the liquid polymer. In some aspects, the mixture may be molded by a transfer molding process or by extrusion (e.g., through a tube).

The therapeutically active agent (e.g., enzalutamide) may be provided in the mixture in an amount such that a total amount of active agent in the implant may be from about 0.5% w/w to about 80% w/w, for example, about 0.5% w/w, about 1% w/w, about 5% w/w, about 10% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, about 70% w/w, about 75% w/w, or about 80% w/w. In some cases, the total amount of active agent (e.g., enzalutamide) in the implant may be at least about 0.5% w/w, at least about 1% w/w, at least about 5% w/w, at least about 10% w/w, at least about 15% w/w, at least about 20% w/w, at least about 25% w/w, at least about 30% w/w, at least about 35% w/w, at least about 40% w/w, at least about 45% w/w, at least about 50% w/w, at least about 55% w/w, at least about 60% w/w, at least about 65% w/w, at least about 70% w/w, at least about 75% w/w, or at least about 80% w/w. Enzalutamide may be provided in the mixture in an amount such that a total amount of enzalutamide in the implant may be from about 1 mg to about 10 mg.

In some aspects, the thermomolding comprises heating and molding of the mixture (e.g., transfer molding, extrusion, or another process) at about 150° C. to about 200° C., for example, about 150° C., about 155° C., about 160° C., about 165° C., about 170° C., about 175° C., about 180° C., about 185° C., about 190° C., about 195° C., or about 200° C. The molding temperature generally depends on the polymer material selected. Generally, the molding temperature of the polymer material is selected such that it is lower than the melting temperature of the therapeutically active agent. For a thermoplastic, the mixture is heated for sufficient time to achieve a moldable state prior to molding. In some cases, the mixture is heated from about 3 minutes to about 8 minutes, for example, for about 3 minutes, about 4 minutes, about 5 minutes, about 6 minutes, about 7 minutes, or about 8 minutes. In some cases, the melting temperature of enzalutamide (e.g., about 190° C. to about 192° C.) may be greater than the molding temperature of the silicone.

In some aspects, the mixture may further comprise a solvent. Non-limiting examples of solvents that may be used include pentane, heptane, toluene, dichloromethane, tetrahydrofuran, and hexane. A solvent may be used to, e.g., reduce the viscosity of the liquid polymer. In some aspects, the mixture may be molded by a transfer molding process or by extrusion (e.g., through a tube).

After manufacturing the implant as provided herein, the methods may further comprise performing one or more analyses on the implant. In some cases, the one or more analyses may be differential scanning calorimetry (DSC) (e.g., to determine the rate of curing of the implants and/or to evaluate properties of the drug). In some cases, the one or more analyses may be deployment of the implant into surrogate tissue. In some cases, the one or more analyses may be elution testing (e.g., to assess the rate of elution of drug from the implant). In some cases, the one or more analyses may be in vivo stability testing (e.g., to assess the ability of degradants to penetrate the implant). In some cases, the one or more analyses may be viscometry. In some cases, the one or more analyses may be the use of a rheometer (e.g., to assess the viscosity and curing profile for the formulation). In some cases, the one or more analyses may be high pressure liquid chromatography (e.g., to confirm content uniformity and assess impurities in the drug formulation and the molded implant). In some cases, the one or more analyses may be dynamic mechanical analysis (DMA) (e.g., to assess the mechanical properties of the implant to ensure it can be deployed correctly).

Methods of Treatment

Disclosed herein are methods of treating a disease (or a symptom thereof) in a subject. The terms "treating", "treatment", or "treat" may be used interchangeably herein and refer to providing a therapeutic benefit to a subject in need thereof. For example, treating a disease or disorder includes ameliorating, abrogating, reducing, relieving, or curing the disease or disorder. Treating a disease or disorder also includes ameliorating, abrogating, reducing, relieving, or curing one or more symptoms associated with a disease or disorder. When used in reference to a tumor, treating includes diminishing or reducing the size of the tumor or tumor volume.

In various aspects, the subject may have been diagnosed with, may be suspected of having, or may be at risk of having the disease (or one or more symptoms thereof). In some cases, the methods comprise implanting an implant of the disclosure into a target tissue of a subject. An implant of the disclosure may be implanted into a target tissue by any method. In some cases, the implant may be implanted into a target tissue by a surgical method or a non-surgical method. In some cases, the implant may be implanted using standard surgical tools, for example, tools commonly used for biopsies or brachytherapy. In some cases, the implant may be implanted into a target tissue by use of, e.g., a needle, forceps, a catheter (e.g., with a lumen). For example, in one embodiment, the implant may be implanted into a target tissue by deployment from the lumen of a needle or a catheter. In some cases, the implant may be implanted into a target tissue using a cannula of a prostate biopsy needle. In some cases, the implant may be implanted into a target tissue using a Mick® needle. In some cases, deployment of the implant may be guided by ultrasound. In some cases, the implant may be implanted by transperineal implantation (e.g., by use of a template guided needle). In some cases, the implant may be sterile and disposed within a packaging.

In a non-limiting example, a method of deploying an implant of the disclosure into a target tissue may involve disposing a distal end of an elongate tube into the target tissue (e.g., the prostate or tissue adjacent the prostate). In some cases, the elongate tube may be a needle having a lumen. The elongate tube may have a sharp end such that the distal end of the elongate tube can penetrate the target tissue. In some cases, the distal end of the elongate tube may be disposed through a first portion of a grid (e.g., a guide template) such that a first position of the elongate tube in the subject is determined. The grid may allow for proper placement of the implant into the target tissue. In some cases, a trocar is disposed within the lumen of the elongate tube. The methods may involve inserting the elongate tube (with or without a trocar disposed within a lumen of the elongate tube) into the target tissue. The methods may further involve, when using a trocar, removing the trocar from the lumen of the elongate tube, while maintaining the distal end of the elongate tube within the target tissue. The methods may further involve placing an implant of the disclosure within the lumen of the elongate tube. The implant may be pushed through the lumen of the elongate tube by a blunt-ended rod (e.g., a stylet) that is sized to fit within the lumen of the elongate tube. The stylet may be used to push the implant from a proximal end of the elongate tube to the distal end of the elongate tube. The methods may further involve, while maintaining the stylet in position, removing the elongate tube from the target tissue. As the elongate tube is removed from the target tissue, the stylet may push the implant out of the elongate tube and into the target tissue. The methods may further involve removing both the stylet and the elongate tube together from the target tissue.

In some aspects, the methods may involve implanting more than one implant into a target tissue of the subject. For example, the methods may involve implanting a first implant into a first portion of the target tissue, and a second implant into a second portion of the target tissue. In some cases, the first portion of the target tissue and the second portion of the target tissue may be different. In some cases, the first implant may comprise a first therapeutically active agent (e.g., enzalutamide) and the second implant may comprise a second therapeutically active agent. In some cases, the first therapeutically active agent (e.g., enzalutamide) and the second therapeutically active agent may be the same. In other cases, the first therapeutically active agent (e.g., enzalutamide) and the second therapeutically active agent may be different. In some cases, a grid (e.g., a guide template) may be used to position the first implant within the first portion of the target tissue, and to position the second implant within the second portion of the target tissue. In some cases, the first implant and/or the second implant may be positioned with the use of ultrasound guidance.

In some aspects, the methods may further comprise implanting additional implants into the target tissue. For example, the methods may further comprise implanting a third implant into a third portion of the target tissue, implanting a fourth implant into a fourth portion of the target tissue, implanting a fifth implant into a fifth portion of the target tissue, implanting a sixth implant into a sixth portion of the target tissue, implanting a seventh implant into a seventh portion of the target tissue, implanting an eighth implant into an eighth portion of the target tissue, and so forth. The third, fourth, fifth, sixth, seventh, eighth, or more, therapeutically active agents may each be the same, different, or combinations thereof. In some cases, at least three implants are implanted into a target tissue. For example, at least three implants may be implanted into the prostate or tissue adjacent or near the prostate by transperineal administration.

In some aspects, one or more implants may be implanted into a prostate or tissue adjacent or near a prostate prior to a surgical procedure to treat prostate cancer. For example, one or more implants may be implanted into a prostate or tissue adjacent or near a prostate prior to performing a prostatectomy (e.g., a week before, two weeks before, three weeks before, etc.). In such cases, the prostatectomy may remove the prostate or a portion thereof. In some cases, the prostatectomy may remove one or more of the implants from the subject. In other cases, one or more implants may be implanted into a prostate or tissue adjacent or near a prostate, and may remain in the prostate indefinitely. For example, the one or more implants may provide a therapeutically effective amount of enzalutamide to the prostate tissue for a period of time such that the subject is in remission or cured of the prostate cancer.

The term "subject", as used herein, generally refers to a vertebrate, such as a mammal, e.g., a human. Mammals include, but are not limited to, murines, simians, humans, research animals, farm animals, sport animals, and pets. In some cases, the methods described herein may be used on tissues derived from a subject and the progeny of such tissues. The tissues may be obtained from a subject in vivo. In some cases, the tissues may be cultured in vitro.

In some aspects, the methods provided herein may be used to treat a subject in need thereof. In some cases, the subject may suffer from a disease. In some cases, the subject may be a human. In some cases, the human may be a patient at a hospital or a clinic. In some cases, the subject may be a non-human animal, for example, a non-human primate, a livestock animal, a domestic pet, or a laboratory animal. For example, a non-human animal can be an ape (e.g., a chimpanzee, a baboon, a gorilla, or an orangutan), an old world monkey (e.g., a rhesus monkey), a new world monkey, a dog, a cat, a bison, a camel, a cow, a deer, a pig, a donkey, a horse, a mule, a lama, a sheep, a goat, a buffalo, a reindeer, a yak, a mouse, a rat, a rabbit, or any other non-human animal.

In cases where the subject may be a human, the subject may be of any age. In some cases, the subject may be about 50 years or older. In some cases, the subject may be about 55 years or older. In some cases, the subject may be about 60 years or older. In some cases, the subject may be about 65 years or older. In some cases, the subject may be about 70 years or older. In some cases, the subject may be about 75 years or older. In some cases, the subject may be about 80 years or older. In some cases, the subject may be about 85 years or older. In some cases, the subject may be about 90 years or older. In some cases, the subject may be about 95 years or older. In some cases, the subject may be about 100 years or older. In some cases, the subject may be about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or greater than 100 years old. In some cases, the subject may be about 1, 2, 3, 4, 5, 6, 7, 8, 9, 10, 11, 12, 13, 14, 15, 16, 17, 18, 19, 20 or greater than 20 years old.

In some cases, the methods provided herein may treat a disease in a subject. In some cases, the methods provided herein may alleviate or reduce a symptom of a disease. In some cases, the methods provided herein may result in a reduction in the severity of one or more symptoms associated with a disease. In some cases, the methods provided herein may slow, halt, or reverse the progression of one or more symptoms associated with a disease. In some cases, the methods provided herein may prevent the development of one or more symptoms associated with a disease. In some cases, the methods provided herein may slow, halt, or reverse the progression of a disease, as measured by the number and severity of symptoms experienced.

In some cases, the disease may be a proliferative disease or disorder. In some cases, the proliferative disease or disorder may be cancer. In some cases, the subject may have a tumor. In some cases, the methods may reduce the size of a tumor. In some cases, the methods may reduce the size of a tumor by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or by about 100%.

In some aspects, the proliferative disease or disorder may be a proliferative disease or disorder of the prostate. In one non-limiting example, the proliferative disease or disorder of the prostate may be prostate cancer. Prostate cancer can be adenocarcinoma, sarcoma, neuroendocrine tumors, small cell carcinoma, transitional cell carcinoma, or squamous cell carcinoma. In some cases, the prostate cancer is castration-sensitive prostate cancer or non-metastatic castration-resistant prostate cancer. In another non-limiting example, the proliferative disease or disorder of the prostate may be benign prostatic hyperplasia.

The methods may be employed to deliver a therapeutically effective amount of enzalutamide to a target tissue. In some cases, the methods may involve delivering a drug implant to a target tissue (or a tissue adjacent to the target tissue) of the subject. Any tissue may be suitable for delivery of a drug implant of the disclosure. In exemplary cases, the target tissue may be the prostate, tissue adjacent to the prostate, or both. Non-limiting examples of target tissue includes breast, pancreas, bladder, brain, skin, kidney, lung, liver, tongue, esophagus, stomach, intestine, gallbladder, heart, pituitary gland, pineal gland, thyroid gland, parathyroid gland, adrenal gland, eye, bone, fallopian tubes, uterus, ovary, sinuses, inner ear (eustachian tube), testes, and neck.

In various aspects of the disclosure, the methods provide for implanting a drug implant of the disclosure into the target tissue (or an adjacent tissue) of a subject, wherein the implant delivers a therapeutically effective amount of enzalutamide to the target tissue. As used herein, a "therapeutically effective amount" when used in reference to a drug or therapeutically active agent refers to an amount of drug or therapeutically active agent that is capable of eliciting a therapeutic response in a subject. In various aspects of the disclosure, the implant may deliver a therapeutically effective amount of drug to a tissue of the subject from 6 months to 24 months. In some cases, the implant may deliver a therapeutically effective amount of drug to a tissue of the subject for 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, or 24 months. In some cases, the implant may deliver a therapeutically effective amount of drug to a tissue of the subject for at least 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months, at least 23 months, or at least 24 months.

In various aspects of the disclosure, a therapeutically effective amount of drug may be at least about 0.1 µg/day. In some cases, a therapeutically effective amount of drug may be at least about 0.1 µg/day, about 0.2 µg/day, about 0.3 µg/day, about 0.4 µg/day, about 0.5 µg/day, about 0.6 µg/day, about 0.7 µg/day, about 0.8 µg/day, about 0.9 µg/day, about 1 µg/day, about 2 µg/day, about 3 µg/day, about 4 µg/day, about 5 µg/day, about 6 µg/day, about 7 µg/day, about 8 µg/day, about 9 µg/day, about 10 µg/day, about 15 µg/day, about 20 µg/day, about 25 µg/day, about 30 µg/day, about 35 µg/day, about 40 µg/day, about 45 µg/day, about 50 µg/day, about 55 µg/day, about 60 µg/day, about 65 µg/day, about 70 µg/day, about 75 µg/day, about 80 µg/day, about 85 µg/day, about 90 µg/day, about 95 µg/day, about 100 µg/day, about 110 µg/day, about 120 µg/day, about 130 µg/day, about 140

μg/day, about 150 μg/day, about 160 μg/day, about 170 μg/day, about 180 μg/day, about 190 μg/day, about 200 μg/day, about 210 μg/day, about 220 μg/day, about 230 μg/day, about 240 μg/day, about 250 μg/day, about 260 μg/day, about 270 μg/day, about 280 μg/day, about 290 μg/day, about 300 μg/day, about 310 μg/day, about 320 μg/day, about 330 μg/day, about 340 μg/day, about 350 μg/day, about 360 μg/day, about 370 μg/day, about 380 μg/day, about 390 μg/day, about 400 μg/day, about 410 μg/day, about 420 μg/day, about 430 μg/day, about 440 μg/day, about 450 μg/day, about 460 μg/day, about 470 μg/day, about 480 μg/day, about 490 μg/day, about 500 μg/day, about 510 μg/day, about 520 μg/day, about 530 μg/day, about 540 μg/day, about 550 μg/day, about 560 μg/day, about 570 μg/day, about 580 μg/day, about 590 μg/day, about 600 μg/day, about 610 μg/day, about 620 μg/day, about 630 μg/day, about 640 μg/day, about 650 μg/day, about 660 μg/day, about 670 μg/day, about 680 μg/day, about 690 μg/day, about 700 μg/day, about 710 μg/day, about 720 μg/day, about 730 μg/day, about 740 μg/day, about 750 μg/day, about 760 μg/day, about 770 μg/day, about 780 μg/day, about 790 μg/day, about 800 μg/day, about 810 μg/day, about 820 μg/day, about 830 μg/day, about 840 μg/day, about 850 μg/day, about 860 μg/day, about 870 μg/day, about 880 μg/day, about 890 μg/day, about 900 μg/day, about 910 μg/day, about 920 μg/day, about 930 μg/day, about 940 μg/day, about 950 μg/day, about 960 μg/day, about 970 μg/day, about 980 μg/day, about 990 μg/day, about 1000 μg/day or greater. It should be understood that a therapeutically effective amount of drug may vary based on the drug and/or the disease to be treated, and may be determined empirically.

In various aspects, the implant may result in cumulative release of enzalutamide from the implant into the target tissue. In some cases, the cumulative release of enzalutamide from the implant in vitro may be at least 140 μg on day 1. In some cases, the cumulative release of enzalutamide from the implant in vitro may be at least 1,000 μg on day 60. In some cases, the cumulative release of enzalutamide from the implant in vitro may be at least 1,500 μg on day 120. In some cases, at least 50% of the total amount of enzalutamide present within the implant at the time of implantation remains in the polymer matrix at 100 days post-implantation. In various aspects, the implant may result in cumulative release of the enzalutamide in an in vitro model of one or more of: no more than 2,000 micrograms by day 1, no more than 12,000 micrograms by day 60, and no more than 16,000 micrograms by day 120. In various aspects, the implant may result in cumulative release of the enzalutamide in an in vitro model of one or more of: at least 10 micrograms by day 1, at least 200 micrograms by day 60, and at least 300 micrograms by day 120. The in vitro model may include incubating the drug implant in 1% sodium dodecyl sulfate (SDS) in water at 37° C. for the specified time period with continuous agitation.

In various aspects of the disclosure, the implant may be configured to remain within the target tissue for a period of time. In some cases, the implant may be configured to remain within the target tissue for long periods of time (e.g., months to years) or indefinitely (e.g., may never be removed). For example, after the implant has delivered all of the therapeutically active agent contained therein to the subject, the implant (devoid of the therapeutically active agent) may remain within the target tissue. In some cases, if additional treatment is needed, one or more additional implants may be delivered to the target tissue (without removing the initial implant). In some cases, the implant may be composed of a non-biodegradable and/or non-resorbable polymer material such that the polymer material remains substantially intact within the target tissue for long periods of time or indefinitely.

Advantageously, the implants of the disclosure are capable of delivering a therapeutically effective amount of enzalutamide to the prostate tissue, or tissue adjacent or near the prostate, for extended periods of time (e.g., at least 6 months). Additionally, the implants of the disclosure are capable of delivering a high concentration of enzalutamide locally to the prostate, while maintaining low systemic concentrations of enzalutamide. In some cases, the implants of the disclosure may reduce or prevent toxicity due to high systemic concentrations of enzalutamide.

In various aspects, a total dose of enzalutamide administered to the subject by an implant of the disclosure is less than a total dose of enzalutamide when administered to a subject by systemic (e.g., oral) administration. Standard oral dosing regimens of enzalutamide include 240 mg/day enzalutamide monotherapy for prostate cancer. Advantageously, the implants of the disclosure provide for administration of lower total doses of enzalutamide relative to oral dosing regimens. In some cases, the total amount of enzalutamide administered to a subject is less than 100 mg over a 6-month period.

In various aspects, implanting a drug implant of the disclosure into the prostate or tissue adjacent or near the prostate results in a blood plasma concentration of enzalutamide that is substantially less than a blood plasma concentration of enzalutamide obtained when enzalutamide is administered to a subject by systemic (e.g., oral) administration. For example, the steady state blood plasma concentration of enzalutamide (assuming 240 mg daily dose) has been reported to be about 6 μg/ml. In some cases, implanting an implant of the disclosure into the prostate or tissue adjacent or near the prostate results in a steady state blood plasma concentration of enzalutamide that is less than 6 μg/ml.

Kits

Further provided herein are kits. In some aspects, a kit may comprise one or more implants as described herein. For example, a kit may include 1, 2, 3, 4, 5, 6, 7, 8, 9, 10, 11, 12, 13, 14, 15, 16, 17, 18, 19, 20 or more than 20 implants. In some cases, the one or more implants may comprise a therapeutically active agent contained therein. In some cases, each of the one or more implants may comprise enzalutamide. In other cases, each of the one or more implants may comprise one or more different therapeutically active agents.

In some aspects, a kit may comprise one or more surgical tools, such as a needle or forceps. In some aspects, a kit may be packaged in a sterilized package. In some cases, the sterilized package comprises a foil. In some aspects, a kit may further comprise instructions for implanting the implant into a tissue of a subject.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed.

In this application, the use of the singular includes the plural unless specifically stated otherwise. It must be noted that, as used in the specification and the appended claims, the singular forms "a," "an", and "the" include plural referents unless the context clearly dictates otherwise. In this application, the use of "or" means "and/or" unless stated otherwise. Furthermore, use of the term "including" as well as other forms, such as "include", "includes", and "included", is not limiting.

As used herein, ranges and amounts can be expressed as "about" a particular value or range. About also includes the exact amount. Hence "about 5 μL" means "about 5 μL" and also "5 μL" Generally, the term "about" includes an amount that would be expected to be within experimental error, e.g., within 15%, 10%, or 5%.

The section headings used herein are for organizational purposes only and are not to be construed as limiting the subject matter described.

EXAMPLES

Example 1. Methods for Making Implants—Acetoxy-Cured Silicone

Manufacture of the implant includes two main steps: formulation of the active pharmaceutical ingredient (API) (e.g., enzalutamide) with an elastomer (e.g., acetoxy-cured silicone) to ensure uniform mixing of the API within the polymer matrix, and molding of the implants to ensure the product can be deployed to the organ as intended.

Formulation

The implant formulation includes medical grade silicone as an excipient mixed with the API. A solvent is used for reducing the viscosity of the silicone, if needed, to incorporate the desired API loading.

The enzalutamide formulation is made using a centrifugal mixer. The required amount of silicone is added to the mixing cup with an equal weight of a solvent (that dissolves silicone; e.g., pentane) added. The silicone and solvent are speed-mixed until the viscosity of the silicone is reduced such that it flows. The API powder is then incorporated into the mixing cup and speed-mixed until a visibly smooth mixture is obtained with no dry API spots. The solvent is then removed (with or without vacuum) leaving a paste of silicone and API. A portion of the solvent (as high as 50% w/w) may be left in the mixture to slow the curing process and extend pot life as well as reduce viscosity to aid in molding or extrusion. Table 1 below shows an example for the formulation of enzalutamide made to 10% load by weight.

This method may be used to formulate active pharmaceutical ingredient (e.g., enzalutamide) with an elastomer (e.g., acetoxy-cured silicone) from as low as 10% load by weight, to above 70% load by weight.

Other methods to achieve the same mix uniformity that are solvent-less may be used, such as shear mixing. Other solvents (e.g., dichloromethane, tetrahydrofuran, hexane, pentane, heptane, toluene, and the like) that aid in reduction of viscosity and dissolve silicone may also be used for formulation.

TABLE 1

| Example Formulation Composition | |
|---|---|
| Component | Weight Added (g) |
| Elkem Silbione ® ADH1 M200 | 1 |
| Solvent | 1 |
| Enzalutamide Milled Powder | 0.1 |

Molding

Implant rods are made by extruding the enzalutamide formulation (e.g., through a tube). The molded rods are cured for a predetermined time (about 1-3 days) at an ambient temperature to ensure the silicone has cured. Post-curing, the rods are pulled out of the tubing and cut to length, and are characterized.

Example 2. Methods for Making Implants—Thermoplastic Polyurethane Solvent Process In this example, the implant formulation includes thermoplastic polyurethane as an excipient mixed with the API.

Formulation

A solvent is used for dissolution of the polyurethane to allow compounding with the API to create a uniform dispersion at the desired loading. After compounding, the solvent is removed and the resulting polyurethane-API pellet is molded into implant rods by transfer molding or extrusion.

The polyurethane pellets are added to a mixing cup with solvent (e.g., dichloromethane) and incubated at 37° C. with agitation for several hours until dissolution of the polyurethane is achieved. The ratio of polyurethane to solvent is selected to achieve full dissolution of the polyurethane and a solution of sufficiently low viscosity for mixing (e.g., about 20% solids content by weight). The API powder is then added to the solution and speed-mixed until a visibly smooth mixture is obtained with no dry API spots. Table 2 below shows an example for a formulation made with 30% API w/w. The solvent is then removed under vacuum leaving a large pellet consisting of polyurethane, API, and residual solvent that may be used for thermomolding. Table 3 below shows an example set of solvent removal conditions. Other solvents (e.g., tetrahydrofuran, dimethylformamide, dimethylacetamide, etc.) that dissolve polyurethane may also be used for formulation.

TABLE 2

| Example Formulation Composition | |
|---|---|
| Component | Weight Added (g) |
| Lubrizol Pathway PT-87AS | 1 g |
| Solvent | 6 g |
| Enzalutamide Milled Powder | 0.45 g |

TABLE 3

| Example Solvent Removal Conditions | | | | |
|---|---|---|---|---|
| Solvent Removal Cycle | Step | Speed (RPM) | Time (min) | Vacuum (psi) |
| 1 | 1 | 950 | 1.8 | 9.0 |
|  | 2 | 950 | 0.3 | 14.7 |
|  | 3 | 1450 | 1.8 | 3.9 |
| 2 | 1 | 1950 | 2.8 | 3.9 |
|  | 2 | 1950 | 2.8 | 3.9 |
|  | 3 | 1950 | 2.8 | 3.9 |
|  | 4 | 1950 | 2.8 | 3.9 |
| 3 | 1 | 800 | 2.8 | 0.14 |
|  | 2 | 2400 | 0.3 | 0.14 |
|  | 3 | 950 | 2.8 | 0.14 |

Molding

Implant rods are made using a (e.g., aluminum) mold (e.g., via a transfer molding process) or by extruding the enzalutamide formulation (e.g., through a tube). The formulation is melted for several minutes (about 3 to 8 minutes) at a certain temperature (about 150° C. to 200° C.) before injection or extrusion. Post-curing, the mold is cooled, and the rods are de-molded for characterization.

Example 3. Methods for Making Implants—Thermoplastic Polyurethane and Polyethylene Vinyl Acetate Extrusion Process In this example, the implant formulation includes thermoplastic polyurethane or polyethylene vinyl acetate as an excipient mixed with the API.

Formulation

Milled excipient powder (thermoplastic polyurethane or polyethylene vinyl acetate) is added to the mix cup along with the API (Enzalutamide). The cup is speed-mixed until powders are fully incorporated. Table 4 below shows typical measurements for a 2-gram powder mix at 50% API load by weight. Ratios are adjusted for different targeted loads.

TABLE 4

Example Formulation Composition—50% Enzalutamide load by weight

| Component | Weight Added (g) |
|---|---|
| Lubrizol Pathway PT-87AE cryo milled | 1 g |
| Enzalutamide Milled Powder | 1 g |

Molding

Implant rods are made with an extrusion process. An aliquot of the powder mix (0.5-1 g) is placed in the cavity of a custom-designed extrusion fixture, compatible with a Rolenn press. The plunger is then placed in the cavity, and the fixture is placed in the press. The press clamps down to heat the aliquot of mix to approximately 150° C. for 1-3 minutes. The transfer pressure is activated to push the plunger into the cavity, forcing the melted powder mix through the extrusion nozzle on the side of the fixture. The nozzle diameter can be adjusted to obtain an implant of a certain diameter. As the extruded rope leaves the fixture, it is collected. After it has cooled for a few seconds, it can be cut to desired lengths for implant rods.

This process can be completed with powder mixes containing a milled excipient and API powder, or even pellets from solvent mixes as described herein.

Example 4. Characterization of Enzalutamide Containing Formulation and Implants Various analytical techniques are used for characterization of the formulation and molded implants. Differential Scanning calorimetry (DSC) is used to e.g., determine the rate of curing of the implants and to evaluate properties of the drug. Elution testing is used to assess the rate of elution of drug from the implant. High Pressure Liquid Chromatography (HPLC) is used to e.g., confirm content uniformity and assess impurities in the drug formulation and molded rods.

Example 5. Elution Testing of Various Drug Implants of the Disclosure

Elution testing was performed on various drug implants according to embodiments provided herein. Three groups of polymers were tested with enzalutamide: silicone with acetoxy-cure system (Elkem M200), thermoplastic polyurethane (Lubrizol Pathway), and ethylene vinyl acetate (Celanese ATEVA) according to Table 5 below. Several percentages of vinyl acetate were tested (10%, 28%, 40%). Drug implants were made according to Examples 1-3 above.

TABLE 5

Summary of polymers and enzalutamide loads for elution testing

| Polymer | Enzalutamide Load |
|---|---|
| Silicone (M200) | 10%, 70% |
| TPU 16HRLN | 10%, 70% |
| PEVA 10% vinyl acetate | 50% |
| PEVA 28% vinyl acetate | 10%, 70% |
| PEVA 40% vinyl acetate | 50% |

Figure 1B:
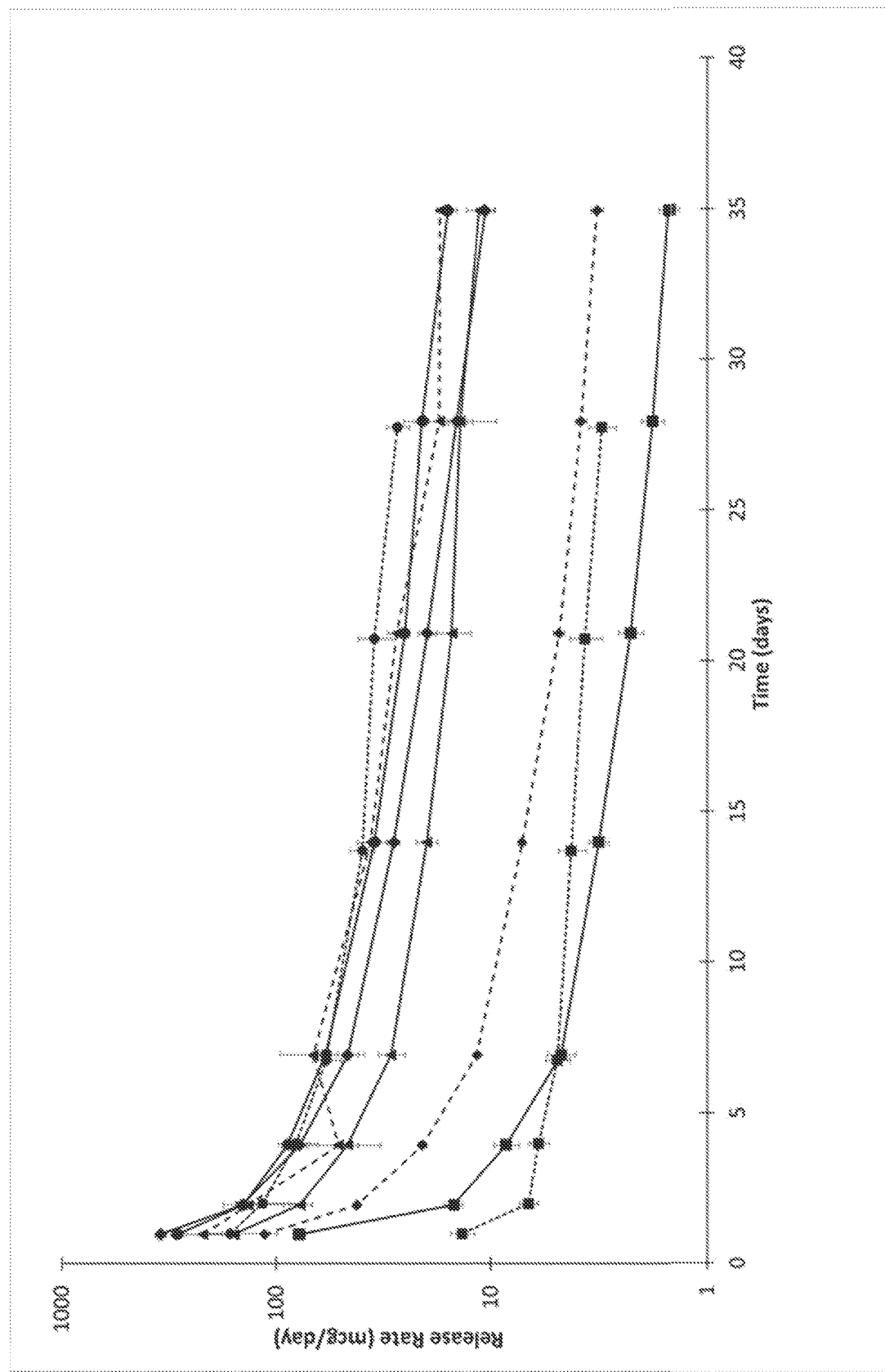
FIG. 1B depicts release rate data for drug implants containing enzalutamide at various loading amounts in accordance with embodiments provided herein.
Figure 2A:
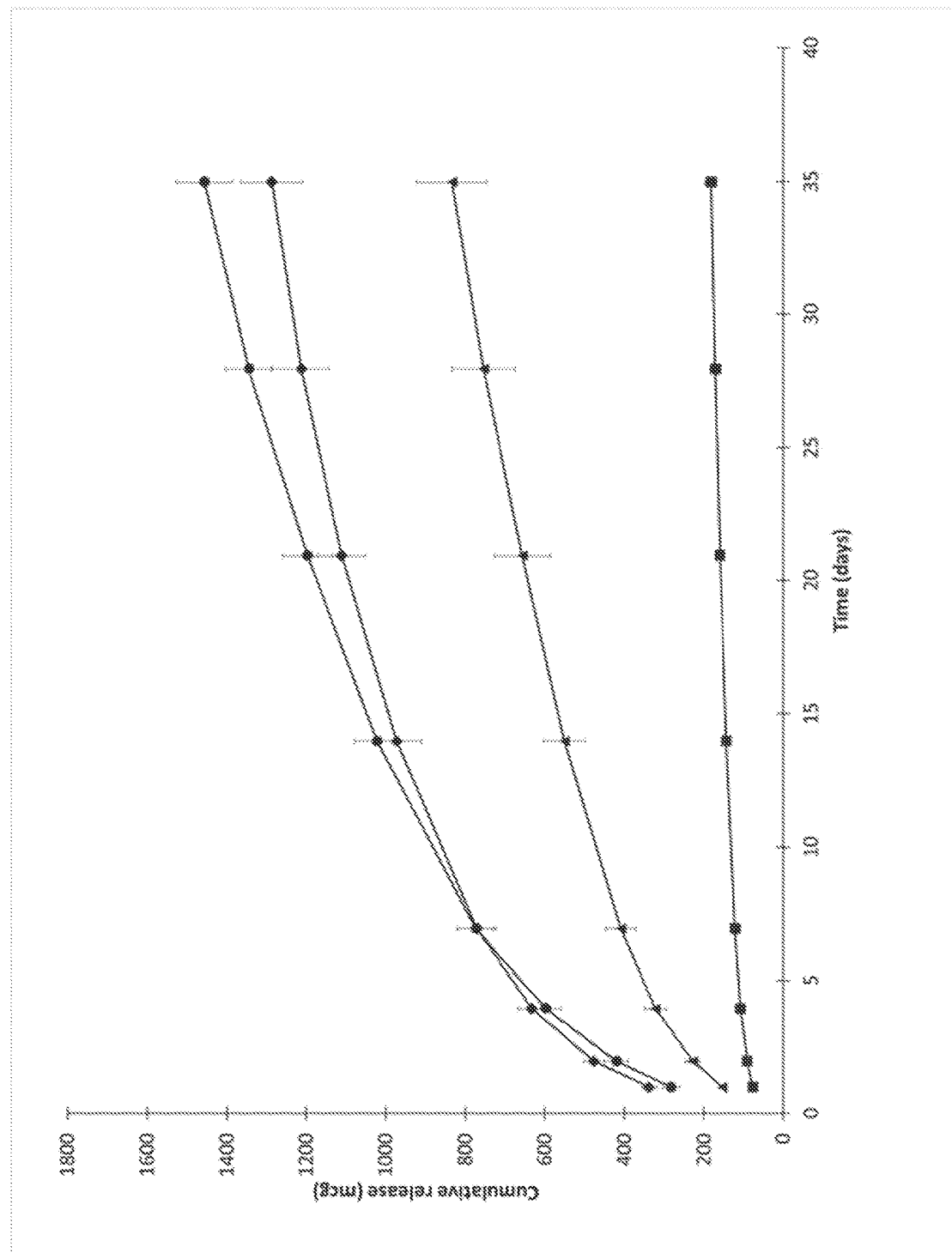
FIG. 2A depicts cumulative release data for various poly(ethylene vinyl acetate) drug implants containing enzalutamide in accordance with embodiments provided herein.
Figure 2B:
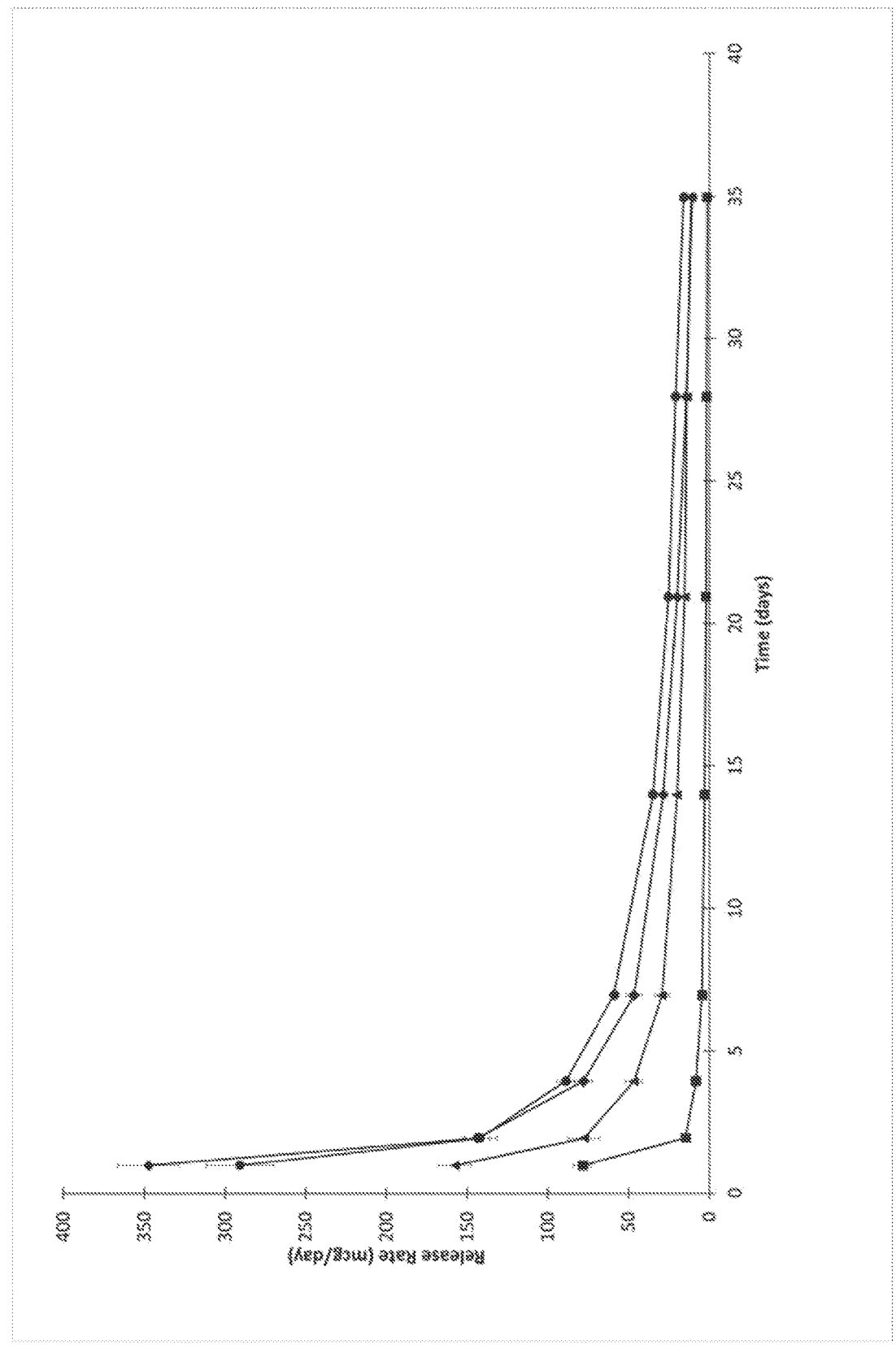
FIG. 2B depicts release rate data for various poly(ethylene vinyl acetate) drug implants containing enzalutamide in accordance with embodiments provided herein.
Figure 3A:
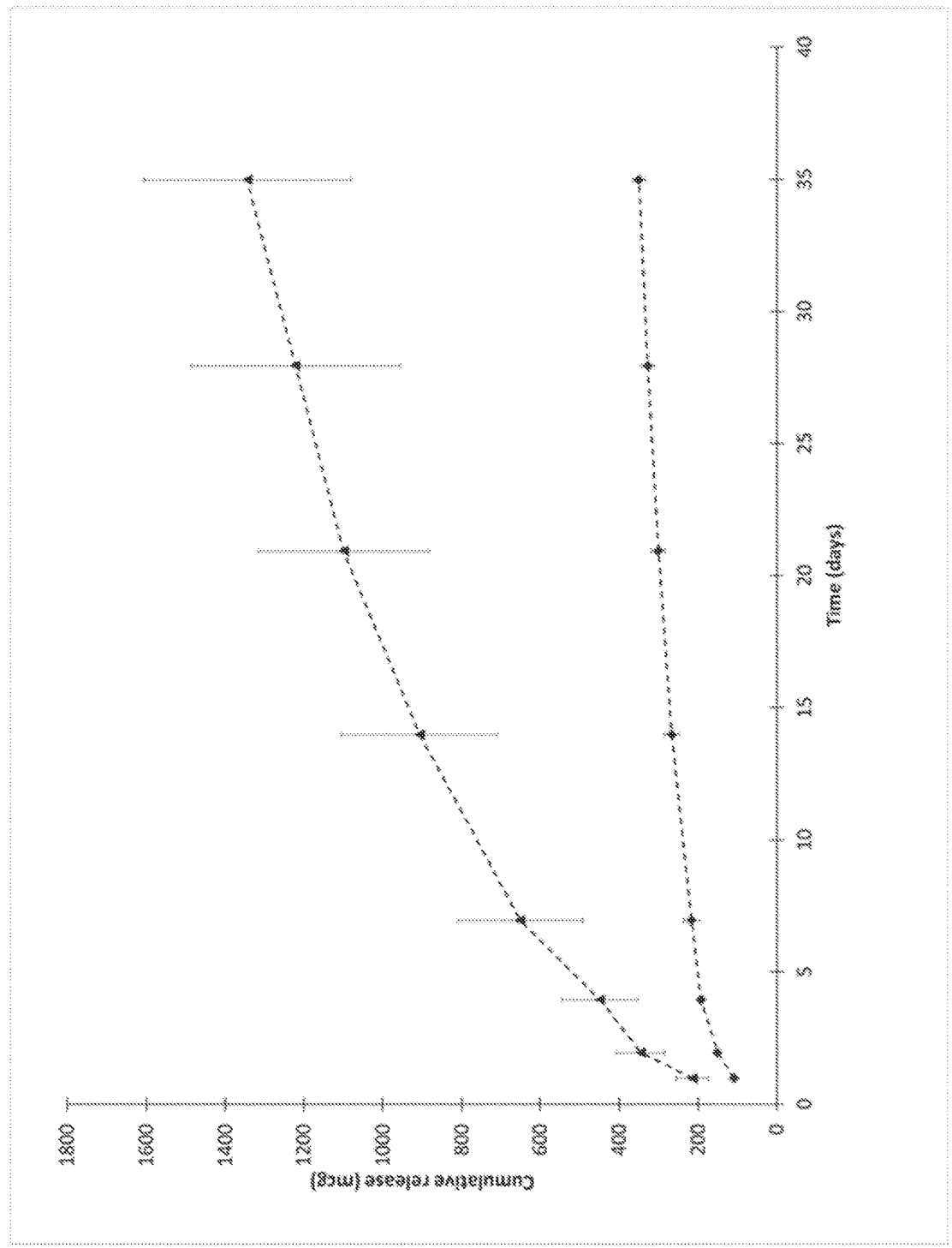
FIG. 3A depicts cumulative release data for various thermoplastic polyurethane drug implants containing enzalutamide in accordance with embodiments provided herein.
Figure 3B:
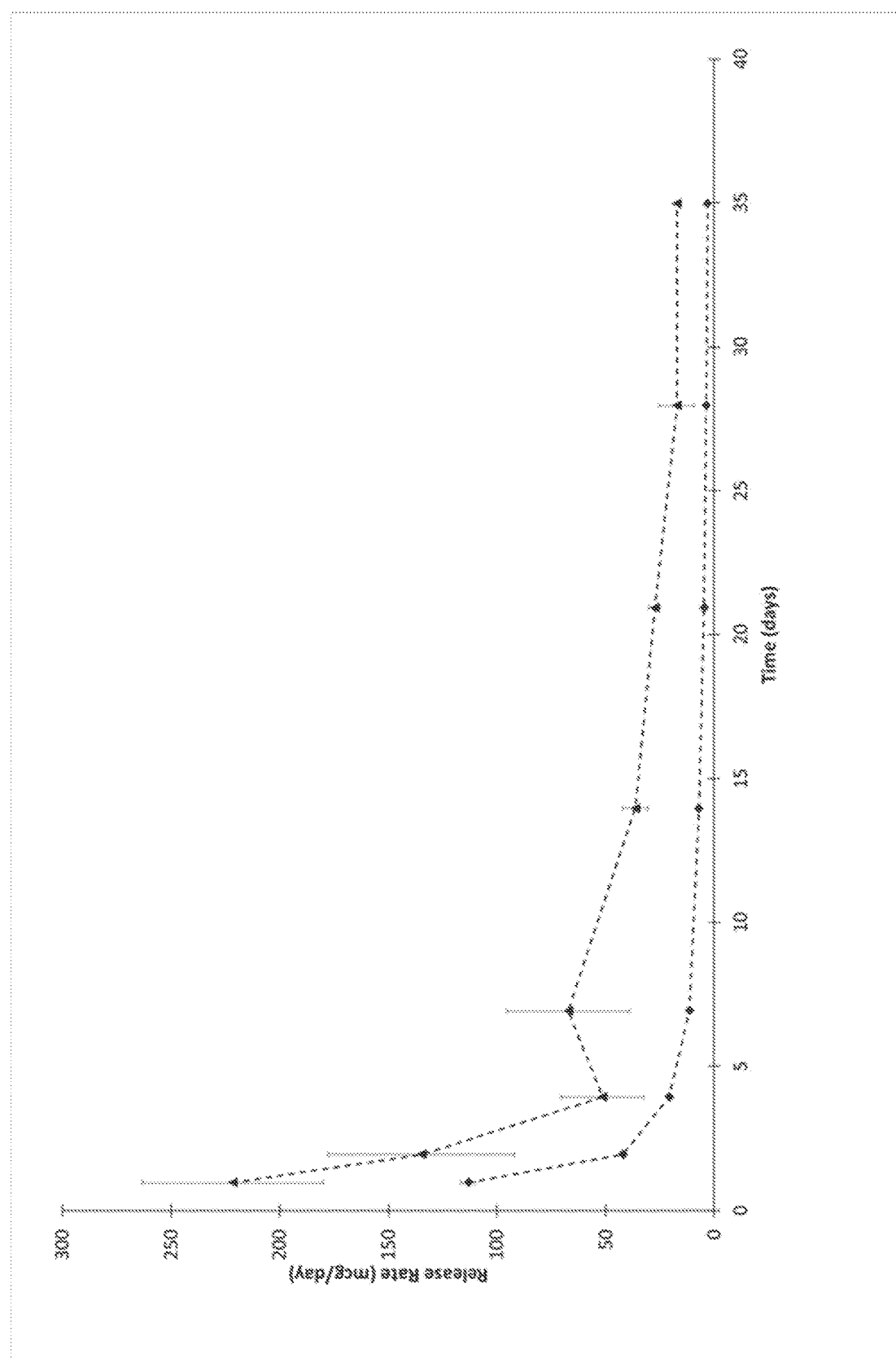
FIG. 3B depicts release rate data for various thermoplastic polyurethane drug implants containing enzalutamide in accordance with embodiments provided herein.
Figure 4A:
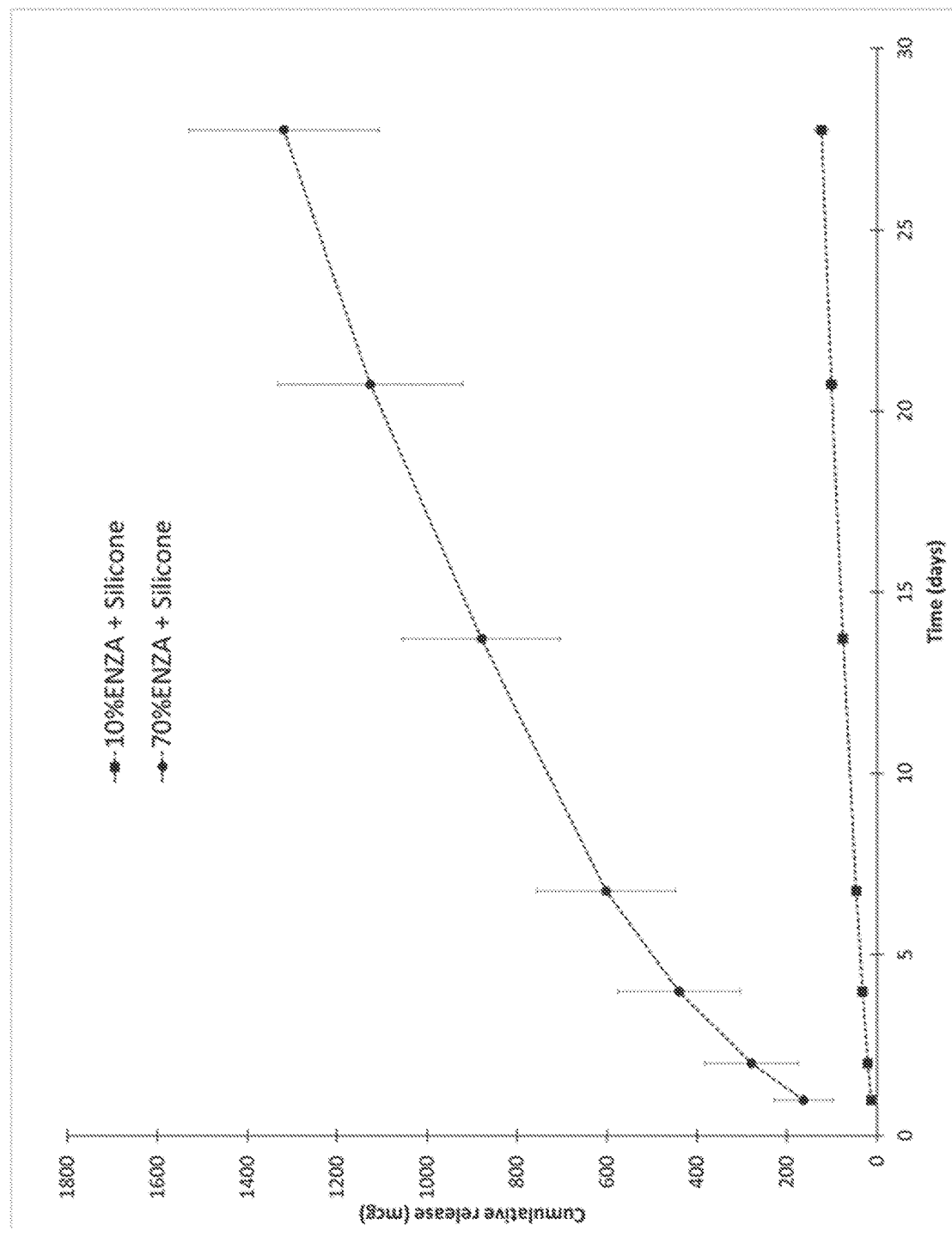
FIG. 4A depicts cumulative release data for acetoxy-cured silicone drug implants containing enzalutamide in accordance with embodiments provided herein.
Figure 4B:
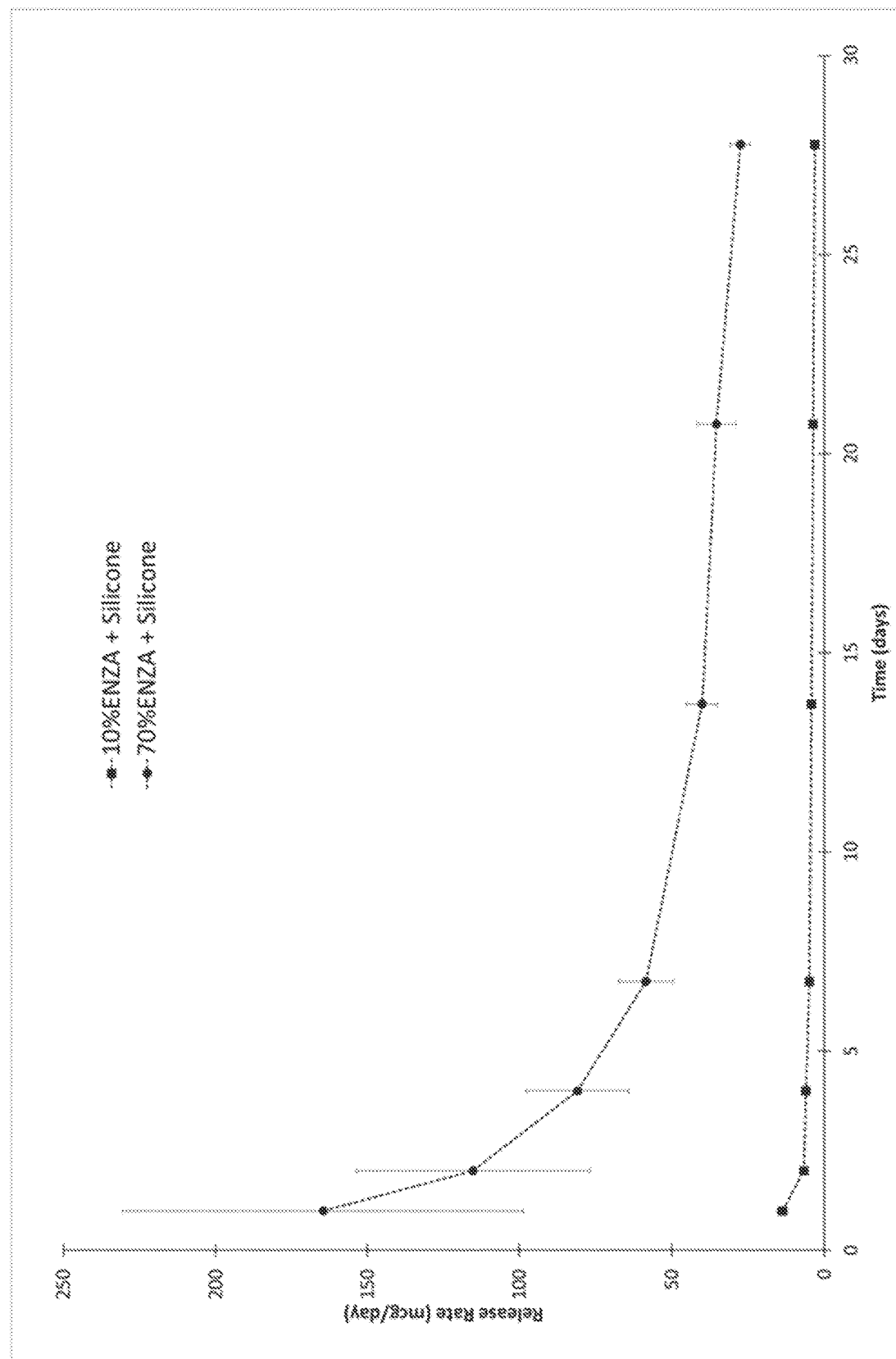
FIG. 4B depicts release rate data for acetoxy-cured silicone drug implants containing enzalutamide in accordance with embodiments provided herein.

Drug implants were incubated in 1% sodium dodecyl sulfate in water at 37° C. for up to 35 days. FIGS. 1A and 1B depict release rates and cumulative release of enzalutamide from various drug implants. FIGS. 2A and 2B depict release rates and cumulative release of enzalutamide from ethylene vinyl acetate implants. FIGS. 3A and 3B depict release rates and cumulative release of enzalutamide from thermoplastic polyurethane implants. FIGS. 4A and 4B depict release rates and cumulative release of enzalutamide from acetoxy-cured silicone implants.

Figure 5:
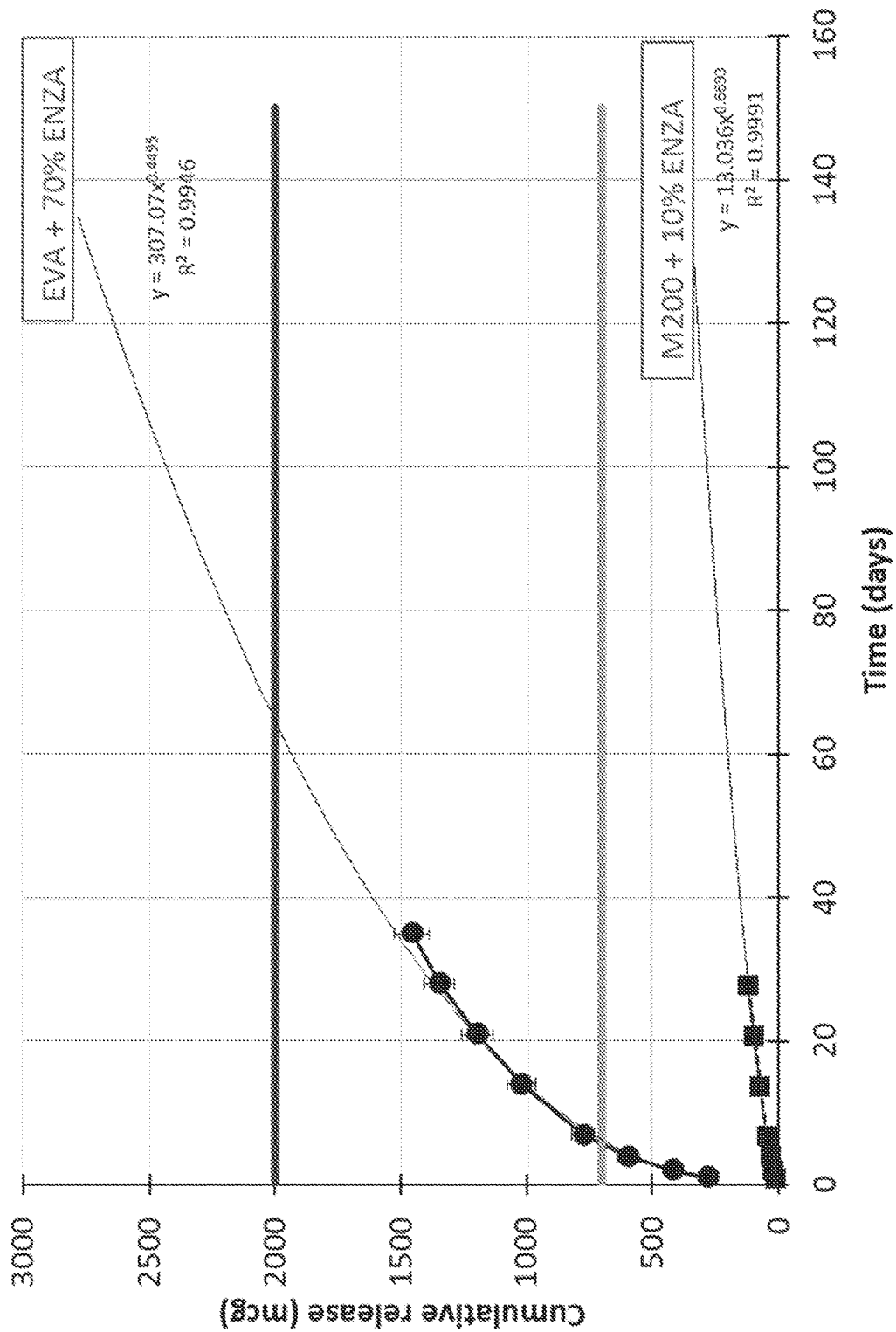
FIG. 5 depicts modeling of cumulative release amounts for poly(ethylene vinyl acetate) and acetoxy-cured silicone drug implants containing enzalutamide in accordance with embodiments provided herein.

Elution modeling was also performed. Data were fitted to a power curve to project future elution rates. FIG. 5 depicts projected elution rates of enzalutamide for silicone and ethylene vinyl acetate drug implants. The horizontal lines show the total enzalutamide load for each test formulation. Table 6 below summarizes the elution modeling data.

TABLE 6

| | Projected elution rates | | | | | | | |
|---|---|---|---|---|---|---|---|---|
| | Cumulative release fit | | Cumulative release by day (mcg) | | | | | |
| Formulation | Coef | exp | 1 | 7 | 14 | 30 | 60 | 120 |
| | (a) | (b) | | | | | | |
| Silicone + 10% Enzalutamide | 13.04 | 0.67 | 13 | 48 | 76 | 127 | 202 | 321 |
| EVA(28) + 70% Enzalutamide | 307.07 | 0.45 | 307 | 736 | 1006 | 1416 | 1934 | 2641 |
| High formulation scaled 6x* | | | 1842 | 4418 | 6034 | 8499 | 11606 | 15848 |

*Implants were tested at 0.5 cm length. A 6 x scaling factor was applied to model elution rates of a 3 cm length implant.

What is claimed is:

1. A drug implant comprising:
   a) a biocompatible, non-biodegradable polymer matrix; and
   b) enzalutamide dispersed in the biocompatible, non-biodegradable polymer matrix.

2. The drug implant of claim 1, wherein the enzalutamide is present in the drug implant at an amount from about 10% w/w to about 80% w/w.

3. The drug implant of claim 2, wherein a total dose of the enzalutamide in the drug implant is from about 1 mg to about 10 mg.

4. The drug implant of claim 1, wherein the drug implant releases at least about 0.1 μg/day of the enzalutamide at 6 months after implantation in a subject.

5. The drug implant of claim 1, wherein cumulative release of the enzalutamide in an in vitro model is
  (i) no more than 2000 micrograms by day 1, no more than 12,000 micrograms by day 60, and no more than 16,000 micrograms by day 120; and is
  (ii) at least 10 micrograms by day 1, at least 200 micrograms by day 60, and at least 300 micrograms by day 120,
  wherein the in vitro model comprises incubation of the drug implant in 1% sodium dodecyl sulfate in water at 37° C. with continuous agitation.

6. The drug implant of claim 1, wherein the biocompatible, non-biodegradable polymer matrix is an acetoxy-cured silicone.

7. The drug implant of claim 1, wherein the biocompatible, non-biodegradable polymer matrix is a thermoplastic polyurethane or poly(ethylene vinyl acetate).

8. The drug implant of claim 1, wherein at least 50% of the enzalutamide remains in the biocompatible, non-biodegradable polymer matrix after 100 days of implantation.

9. The drug implant of claim 1, wherein at least 99% by weight of the biocompatible, non-biodegradable polymer matrix remains in a target tissue of a subject after implantation for at least 600 days.

10. The drug implant of claim 1, wherein the enzalutamide is in solid form.

11. The drug implant of claim 1, wherein the enzalutamide is in a crystalline form, a semi-crystalline form, or an amorphous form.

12. The drug implant of claim 1, wherein the drug implant has a Shore A hardness of at least 20 durometer when loaded with 60% w/w of the enzalutamide.

13. The drug implant of claim 1, wherein the drug implant is visible by ultrasound when disposed in a target tissue of a subject.

14. The drug implant of claim 1, wherein the enzalutamide has a melting temperature that is greater than a molding or curing temperature of the polymer matrix.

15. The drug implant of claim 1, wherein the drug implant inhibits modulation of the enzalutamide within the drug implant.

16. The drug implant of claim 15, wherein the modulation comprises degradation.

17. The drug implant of claim 1, wherein a volume of the drug implant is from about 0.1 $mm^3$ to about 30 $mm^3$.

18. The drug implant of claim 1, wherein at least 50% of an outer surface of the drug implant is configured to directly contact a target tissue.

19. The drug implant of claim 1, wherein the drug implant is configured to be implanted into a target tissue or a tissue near or adjacent to the target tissue.

20. The drug implant of claim 19, wherein the target tissue is prostate tissue.

21. The drug implant of claim 1, consisting essentially of the biocompatible, non-biodegradable polymer matrix and the enzalutamide dispersed in the biocompatible, non-biodegradable polymer matrix.

* * * * *

UNITED STATES PATENT AND TRADEMARK OFFICE
CERTIFICATE OF CORRECTION

| | | |
|---|---|---|
| PATENT NO. | : 11,666,528 B2 | Page 1 of 1 |
| APPLICATION NO. | : 17/728702 | |
| DATED | : June 6, 2023 | |
| INVENTOR(S) | : Maithili Rairkar et al. | |

It is certified that error appears in the above-identified patent and that said Letters Patent is hereby corrected as shown below:

In the Specification

Column 1, Line 11, please add --This invention was made with government support under R43 CA257773, and R43 CA281493 awarded by the National Institutes of Health. The government has certain rights in the invention--.

Signed and Sealed this
Sixteenth Day of September, 2025

Coke Morgan Stewart
*Acting Director of the United States Patent and Trademark Office*